Figure 1:
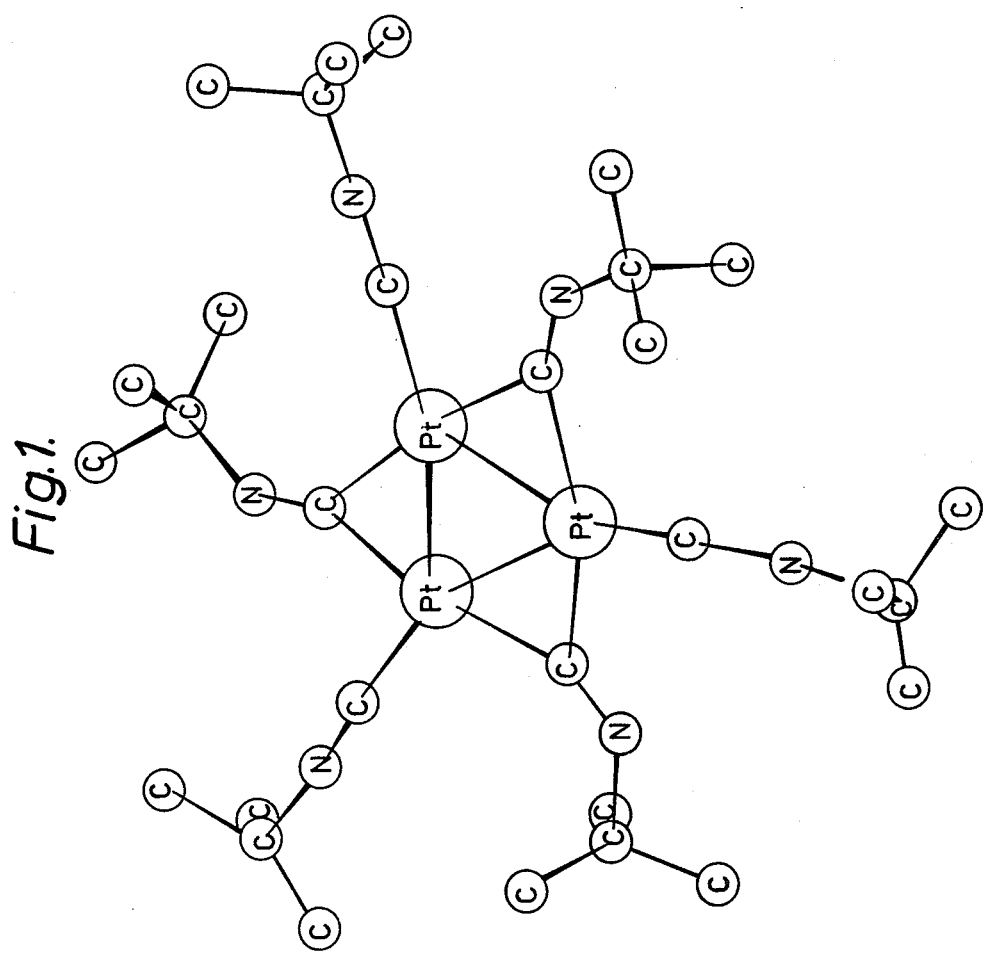

United States Patent [19]

Stone et al.

[11] 4,098,807

[45] Jul. 4, 1978

[54] PLATINUM AND PALLADIUM COMPLEXES

[75] Inventors: Francis Gordon Albert Stone; Michael Green, both of Bristol; John Lionel Spencer, Horfield, all of England

[73] Assignee: Air Products and Chemicals, Inc., Allentown, Pa.

[21] Appl. No.: 641,407

[22] Filed: Dec. 17, 1975

[30] Foreign Application Priority Data

Dec. 9, 1974 [GB] United Kingdom ............... 53120/74
May 12, 1975 [GB] United Kingdom ............... 19837/75

[51] Int. Cl.$^2$ ............................................. C07F 15/00
[52] U.S. Cl. ......................... 260/429 CY; 260/429 R; 260/429 J; 260/441; 260/446; 106/1.24; 106/1.28
[58] Field of Search ................... 260/429 R, 441, 446

[56] References Cited

PUBLICATIONS

Malatesta et al., J. Chem. Soc., p. 2080 (1963).
Malatesta et al., Zerovalent Compounds of Metals, Academic Press N.Y., pp. 154 to 163 (1974).
Cotton, Prog. in Inorg. Chem., Interscience Publ., Inc., N.Y., vol. 1, pp. 366–375 (1959).
Maitlis, The Organic Chemistry of Palladium, Academic Press, N.Y., pp. 14 & 15 (1971).

*Primary Examiner*—Helen M. S. Sneed
*Attorney, Agent, or Firm*—Thomas G. Ryder; E. Eugene Innis; H. Barry Moyerman

[57] ABSTRACT

A method of preparing bis(cis,cis-cyclo-octa-1,5 diene) platinum and palladium by reducing [Pt Cl$_2$(1,5-C$_8$H$_{12}$)] or [Pd Cl$_2$(1,5-C$_8$H$_{12}$)] in the presence of a solvent not having an active hydrogen atom, methods of preparing various other platinum and palladium compounds, some of which are novel from bis(cis,cis-cyclo-octa-1,5 diene) platinum and palladium, and methods of depositing films of platinum or palladium metal on a substrate by coating the substrate with various platinum or palladium compounds which are then decomposed.

10 Claims, 4 Drawing Figures

PLATINUM AND PALLADIUM COMPLEXES

This invention relates to a novel method of preparing bis (cis, cis-cyclo-octa-1,5 diene) platinum and palladium, to several new classes of platinum and palladium compounds which can conveniently be prepared from them or otherwise and which have possible applications in homogeneous catalysis, and to new methods of making certain known platinum and palladium compounds from them. The invention further relates to novel methods of depositing a thin film of metallic platinum or palladium on a substrate, to form a catalyst useful in heterogeneous catalysis.

According to one aspect of the invention we provide a method of preparing bis (cis,cis-cyclo-octa-1,5 diene) platinum or palladium in which a reducing agent is allowed to react with $[PtCl_2 (1,5 - C_8H_{12})]$ or $[PdCl_2 (1,5-C_8H_{12})]$ and excess cis, cis-cyclo-octa-1,5 diene in the presence of a solvent not having an active hydrogen atom.

One preferred reducing agent is the lithium derivative of cyclo-octa-1,3,5,7-tetraene ($Li_2C_8H_8$), in which case diethyl ether is a preferred solvent. Examples of other possible reducing agents are alkali metal naphthalides, lithium metal in pyridine as solvent, and $NaH_2Al(OCH_2CH_2OMe)_2$.

Bis (cis,cis-cyclo-octa-1,5 diene) platinum and palladium are convenient starting materials for the preparation of other platinum and palladium compounds.

Novel platinum and palladium compounds which we have prepared from these materials and which are within the scope of this invention are those of the general formulae:

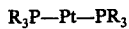

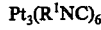

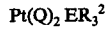

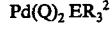

wherein $R_3P—$ is a bulky trisubstituted phosphine group, for example, tricyclohexyl phosphine, $R^1$ is an alkyl or aryl group, Q is a compound which contains at least one olefinic or acetylenic double or triple bond, such as an olefin, allene, acetylene, or substituted olefin, E is P, As, Sb or N and $R^2$ is aryl, alkyl, or alkoxyl. A mixed complex containing those mentioned above can also be prepared.

Novel compounds of the general formula $R_3P—Pt—PR_3$, and known compounds of the formula $R_3P—Pd—PR_3$, can be prepared by treating $Pt(C_8H_{12})_2$ or $Pd(C_8H_{12})_2$, respectively with appropriately substituted bulky phosphine; the phosphine must be bulky so that not more than two of the molecules can form a bond with the Pt atom. The product contains a 14-electron two-coordinate platinum (0) species. $R_3P—Pt—PR_3$ can be converted e.g. with $H_2$ to give the known four coordinate platinum complex -

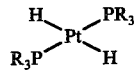

Treatment of $Pt(C_8H_{12})_2$ with the appropriate isonitrile ($R^1NC$) in a solvent such as petroleum ether affords a novel compound of the formula $Pt_3(R^1NC)_6$. This can be converted to a heterocyclic platinum complex by reaction with an electronegatively substituted unsaturated compound e.g. treatment with hexafluoro acetone $(CF_3)_2C=O$ yields the known complex:

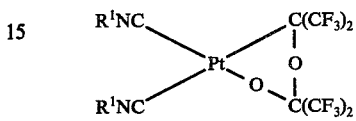

The cyclooctadiene molecules in $PT(C_8H_{12})_2$ and $Pd(C_8H_{12})_2$ can also be replaced by other ethylenically-unsaturated ligands, or acetylenically-unsaturated ligands, e.g. ethylene, butadiene or acetylene, to form the complexes $Pt(Q)_3$ or $Pd(Q)_3$ mentioned above, by reacting them with the appropriate unsaturated compound in a suitably inert solvent e.g. petroleum ether.

These complexes $Pt(Q)_3$ and $Pd(Q)_3$ may also be prepared by reacting $[PtCl_2(1,5-C_8H_{12})]$ or $[PdCl_2(1,5-C_8H_{12})]$ with a reducing agent (e.g. $Li_2C_8H_8$) and the appropriate olefinically or ethylenically unsaturated compound Q. Examples of such compounds which are suitable are bicyclo(2.2.1)heptene.

We further provide novel Pt or Pd complexes of the formulae $Pd(Q)_2ER_3^2$ and $Pt(Q)_2ER_3^2$ in the preparation of which $ER_3^2$ is allowed to react in an inert solvent with $Pd(Q)_3$ or $Pt(Q)_3$.

The complexes $Pt(Q)_3$ and $Pd(Q)_3$ are easily decomposed by heating and thus afford a relatively simple way of depositing a layer of pure platinum or palladium metal on a substrate. For example, trisethylene platinum decomposes to deposit pure platinum, the only other product being $C_2H_4$ which comes off as gas, leaving no impurities in the platinum layer. A convenient way of applying trisethylene platinum to a substrate is in solution form, although as trisethylene platinum is slightly volatile, and as its vapour is stable in a binary mixture with ethylene gas, it may also be deposited from the vapour. A mixture of ethylene and trisethylene platinum is passed over the substrate until the substrate has become coated with the trisethylene platinum. This is then decomposed e.g. either by gentle heating or by passing over the substrate a gas other than ethylene. A platinum layer can also be deposited on a substrate by coating the substrate with cis,cis-cyclo-octa-1,5-diene platinum e.g. in solution form and decomposing it. Our researches indicate that platinum and palladium layers thus deposited have potentially valuable catalytic properties. Thus according to a further feature of the invention we provide a method of forming a catalytically active layer of Pt or Pd metal on a substrate by coating the substrate either with cis,cis-cyclo-octa-1,5-diene platinum or with a complex $Pt(Q)_3$ or $Pd(Q)_3$ in which Q is a compound containing at least one ethylenically or acetylenically unsaturated group, and then heating the coated substrate to decompose the complex.

We also provide a catalyst prepared by any of these methods.

The catalysts have potential applications in heterogeneous catalysis. In addition, all of the above novel Pt and Pd compounds have potential applications in homogeneous catalysis, e.g. in hydrosilation or to trimerise butadiene.

The deposition of Pt or Pd surfaces as described above, especially from the vapour phase, is potentially useful in the manufacture of semiconductors and other electrical devices.

Some specific and more detailed non-limiting examples of the invention will now be given.

All of the crystallographic data in this specification was obtained by single crystal x-ray Crystallography, carried out by Dr. Judith A. Howard at the University of Bristol, England.

EXAMPLE 1

Preparation of cis,cis-cyclo-octa-1,5-diene platinum

A sample of the compound $[PtCl_2(1,5-C_8H_{12})]$ (3.7 g, 10 mmol) was finely powdered and suspended in freshly distilled cis,cis-cyclo-octa-1,5-diene (15 cm$^3$). The mixture was degassed and cooled to $-40°$ C and a solution of the lithium derivative of cyclooctatetraene ($Li_2C_8H_8$) (10 mmol) in diethyl ether was added over 5 minutes. The resulting slurry was allowed to warm to $-10°$ C (1 hr.) and the solvent was evaporated at reduced pressure. Extraction of the residue with dry toluene (5 × 60 cm$^3$ portions) at 0° gave a brown solution which was filtered through a short column (12 cm) of alumina. The volume of solvent was reduced in vacuo to Ca. 20 cm$^3$ and the mother liquor decanted from the white crystalline product, cis,cis-cyclooctal-1,5-diene platinum, (yield 50%).

The $Li_2C_8H_8$ was prepared by suspending lithium foil (1 g.) in dry diethyl ether (80 cm$^3$), cyclo octa-tetraene (3 cm$^3$) was added and the mixture stirred for 16 hr. The resulting solution was standardized by hydrolysis of a known volume and titration with standard aqueous hydrochloric acid. $^1H$ n.m.r. spectrometry on Pt(C$_8$H$_{12}$)$_2$ showed resonances (C$_6$H$_6$) at 5.80 ($J_{HPt}$55Hz) and 7.81.

EXAMPLE 2

Preparation of Pt$_3$(Bu$^t$NC)$_6$

Pt(1,5-C$_8$H$_{12}$)$_2$ was treated with excess Bu$^t$NC in petroleum ether and orange-red crystals of [Pt$_3$(Bu$^t$NC)$_6$] were formed, (infra red bands (Nujol) were found at 2150vs, 2095sh, 1730sh and 1710vs CM$^{-1}$). Analogous complexes have also been prepared in a similar manner in which the tertiary butyl groups are replaced by methyl and cyclohexyl groups. The structure of [Pt$_3$(Bu$^t$NC)$_6$] was determined by single crystal x-ray crystallography.

Crystal Data: monoclinic, P2$_{1/n}$, Z = 4 in a unit cell of dimensions a = 18.213(7), b = 11.811(7), c = 21.966(6) Å; $\beta$ = 110.21(3)°; R = 0.061 for 3680 reflections.

The molecular structure is illustrated in FIG. 1 from which the H atoms have been omitted from the tertiary butyl groups for clarity. This complex crystallises with the inclusion of four molecules of toluene per unit cell: these too have been omitted from the drawing.

The structure consists of an approximately equilateral triangle, mean Pt—Pt distance 2.632 Å, with threee briding and three terminal tertiary-butylisonitrile ligands. The terminal groups form an almost linear Pt—C$_1$—N—C$_2$ chain (mean C$_1$ 176°, mean N 170°), whereas the bridging groups show considerable bending (mean CNC 143°). The bridging carbon atoms lie almost in the plane of the Pt$_3$ triangle, and each are symmetrically related to two Pt atoms, with the errors given, (mean Pt—C bridge distance 2.10 (3) Å, Pt—C—Pt 77°). The nitrogen and distal carbon atoms of these isonitriles show a greater deviation from the plane. The triangular Pt—Pt distance in [Pt$_3$(Bu$^t$NC)$_6$] compares favourably with the average value of 2.65 Å found in the phosphine substituted complexes [Pt$_3$L$_3$($\mu_2$-CO)$_3$](L = phosphine).

Formation in this reaction of a stable Pt$_3$ species is in contrast with the ill defined nature of the related palladium species Pd ($^t$BuNC)$_2$. The cluster of three Pt atoms in this complex in a sense constitutes a Pt surface which suggests that this complex may have valuable catalytic properties. However, it is interesting that the Pt$_3$ array is easily broken in oxidative-addition reaction, for example treatment with hexafluoracetone affords:

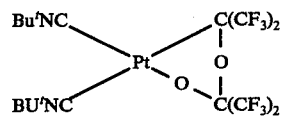

EXAMPLE 3

Preparation of Pt(Q)$_3$ and Pd(Q)$_3$ compounds i.e. trisethylene platinum, trisethylene palladium, tetrafluoroethylene bisethylene platinum, tris(bicyclo(2.2.1) heptene) platinum and palladium Ethylene (at 1 atmosphere, 18° C) displaces the cyclo-octa-1,5,-diene from Pt(C$_8$H$_{12}$)$_2$ in petroleum ether solution to give trisethyleneplatinum as a white crystalline solid (on cooling). This is unstable in solution except under an ethylene atmosphere. The preparation of the corresponding Pd compound is analagous but in this case it is important to ensure that the reaction temperature does not rise above $-20°$ C. $^1H$ n.m.r. spectroscopy of the Pt compound (C$_6$H$_6$, 30° C) shows resonance at 6.83 (J$_{PtH}$57.0 Hz); $^{195}$Pt resonance (INDOR) + 1609 p.p.m. (w.r.t. 21.4 MHz) shows the central 9 lines with the correct relative intensity of the expected 13 line multiplet. In contrast, the recently reported complex [Ni(C$_2$H$_4$)$_3$] is apparently less stable than the platinum analogue and shows a $^1H$ n.m.r. signal ($-30°$ C) at 6.89, which is shifted downfield in the presence of C$_2$H$_4$. It is suggested that trisethylene-platinum has the trigonal-planar structure illustrated in FIG. 2 rather than a structure in which the C:C double bonds are perpendicular to the coordination plane. This assumption which is based on the structure established by x-ray crystallography for tris [bicyclo(2.2.1)heptene] nickel, receives support from a theoretical study of the complexes Ni(C$_2$H$_4$)$_n$ (n = 2,3 or 4).

Since the structural study of the Pt(C$_2$H$_4$)$_3$ presented some difficulties one of the ethylenes was displaced with tetrafluoroethylene in petroleum ether solution to give the more stable species tetrafluoroethylene-bis(ethylene)platinum $^1H$ n.m.r. (CF$_3$F$_6$H$_5$, $-25°$) resonance at 6.60 (s with $^{195}$Pt satellites, J$_{PtH}$45 Hz), $^{19}$F resonance C$_6$D$_6$/toluene $-$ 30°; rel. CCl$_3$F) at 123.6 p.p.m. (s with $^{195}$Pt satellites, J$_{PtF}$248 Hz.), $^{13}$C n.m.r. resonances C$_6$D$_6$/toluene; rel. Me$_4$Si) at $-65.9$ p.p.m. ($^{13}$CH$_2$= CH$_2$, $^1H$ decoupled, J$_{PtC}$284 Hz) and $-100.8$ p.p.m. ($^{13}CF_2 = CF_2$, $^{19}F$ decoupled, $J_{PtC}$470 Hz); at −80° C the $^{13}C$ spectrum was unchanged.

Crystal data: monclinic, A2/a, Z = 4 in a unit cell of dimensions a = 8.884(4), b = 7.552(2), c = 12.934(6) Å; β = 109.51(3)°; R = 0.085 for 765 reflections (Syntex P2$_1$ four circle diffractometer.

Figure 3:
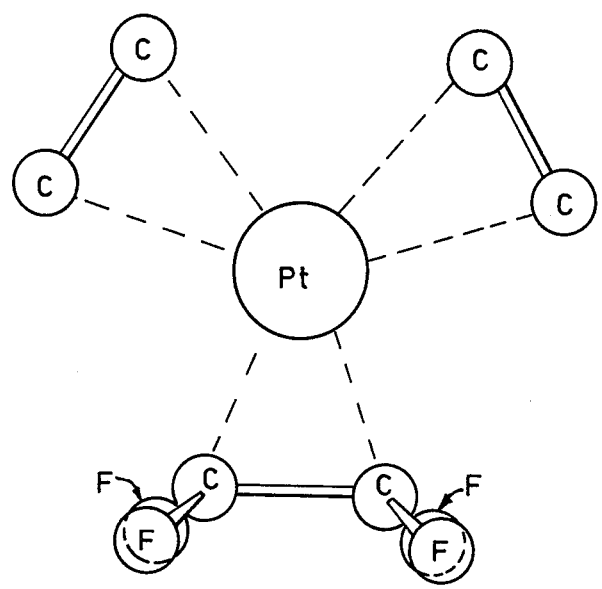

The three olefinic double bonds (see FIG. 3) lie in the coordination plane of the platinum atom with Pt—C distances for Pt—C(F)$_2$ and Pt—C(H)$_2$ at 1.97(3) Å and 2.25(3) Å, respectively. Although within 2 e.s.d.'s of each other at the current stage of refinement the C=C bond lengths reflect the variation in Pt—C distances, being 1.44(4) Å in the coordinated $C_2F_4$ and 1.36(4) in the $C_2H_4$.

In order to confirm the molecular geometry of species Pt(Q)$_3$ and Pd(Q)$_3$ complex tris(bicyclo (2.2.1.) heptene) platinum (white crystals m.p. 144°-145° dec., $^1H$ n.m.r. resonances ($C_6D_6$) at 6.64 (s with $^{195}Pt$ satellites, CH=CH, $J_{PtH}$64 Hz.), 7.04 (s, CH), 8.44 (complex m, CH$_2$.CH$_2$ and 9.76 (AB system, bridging CH$_2$); $^{13}C$ n.m.r. resonances ($C_6D_6$) at −28.6 p.p.m. (H—C, $J_{PtC}$ 44Hz.), −39.5 (bridging CH$_2$, $J_{PtC}$ 49 Hz.) 042.8 (CH$_2$.CH$_2$, $J_{PtC}$14 Hz.) and −68.0 (CH=CH, $J_{PtC}$ 189 Hz.) was synthesized by treating bis(cyclocta-1,5-diene)platinum with bicyclo (2.2.1.)heptene, or more directly by reaction of (PtCl$_2$(1,5-C$_8$H$_{12}$) with Li$_2$C$_8$H$_8$ in Et$_2$O in the presence of excess bicyclo (2.2.1.)heptene.

Figure 4:
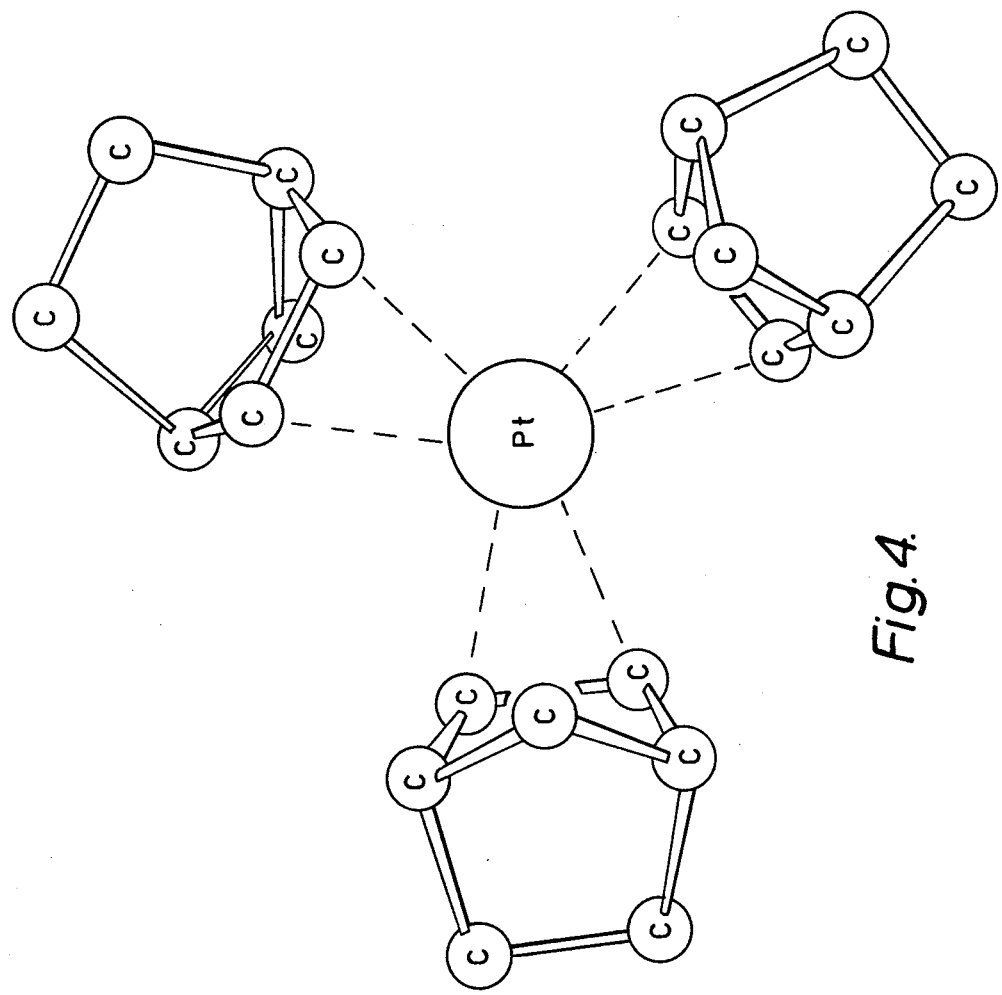

In the molecular structure (see FIG. 4) (Crystal data: orthorhombic, P2$_1$2$_1$2$_1$, Z = 4 in a unit cell of dimensions a = 5.720(1), b = 10.740(4), c = 28.771(12) Å; R = 0.106 for 1695 reflections) the double bonds of the three bicyclo(2.2.1) heptene ligands lie in the coordination plane of the platinum atom, at a mean Pt—C distance of 2.22(3)Å. The maximum deviation from this plane is currently 0.06 Å. The bridgehead carbon atoms C(7) and C(21) lie 2.3 Å to one side of this plane, and the third bridgehead carbon C(14) is 2.3 Å on the opposite side, all lying approximately 3.2 Å from the platinum atom. The C=C bonds have a mean bond length of 1.38(4) Å, which is essentially the same as found for coordinated ethylene. The remaining C—C bond lengths in the coordinated bicyclo (2.2.1)heptene ligands are those expected for singly bonded carbon atoms. The average dihedral angle at the bend of the C$_7$ rings, i.e. between planes C(1)C(2) C(3)C(6) and C(3)C(6)C(5)C(4) etc. is 105°.

A finely powdered sample (1.14g, 4 mmol) of [PtCl$_2$(1,5-C$_8$H$_{12}$)$_2$] in dry diethyl ether was treated with excess bicyclo(2.2.1)heptene. The mixture was de-gassed and cooled to −40° C and a solution of Li$_2$C$_8$H$_8$(4 mmol) in diethl ether was added over 5 minutes. The resultant slurry was warmed to about −10° C and solvent removed at reduced pressure. Extraction of the residue with dry petroleum (10° C) gave a pale solution from which white needles of tris (bicyclo(2.2.1) heptene)palladium (yield 60%) were obtained by cooling to −20° C. In solution this decomposes to palladium metal unless an excess of ligand is present. Crystals of this compound have the same morphology as the analogous platinum compounds, and x-ray photographs indicate they are not only isomorphous but also isostructural. Cell constants are almost identical and the space group is also P2$_1$2$_1$2$_1$ with four molecules per unit cell (a = 5.705(1), b = 10.784(5) and c = 28.770(15)Å).

Thus in both of the 3-coordinate species eterafluoroethylene bis(ethylene) platinum and tris(bicyclo (2.2.1)heptene) platinum where Pt(O) is stabilised by olefinic ligands with different steric and electronic requirements, and also in the case of the Pd(O) complex tris(bicyclo (2.2.1)heptene) palladium, a trigonal planar structure is preferred.

EXAMPLE 4

Preparation of CyP$_3$—Pt—PCy$_3$

Reaction of Pt(C$_8$H$_{12}$)$_2$ with tri-cyclohexylphosphine afforded a 14-electron two coordinate platinum (O) species CyP$_3$—Pt—PCy$_3$, an observation which is of interest in view of recent studies which have established the structural indentity of the analogous palladium species. This complex, which dissolves in toluene to give an orange-yellow solution, reacts (on bubbling) with molecular hydrogen to form a stable dihydride

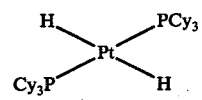

i.r. (Nujol) 1710 cm$^{-1}$, $^1H$ n.m.r. resonance (C$_6$H$_6$) at 13.10 (t with $^{195}Pt$ satellites, $J_{HPt}$2872 Hz), formulated as the trans-isomer.

Figure 2:
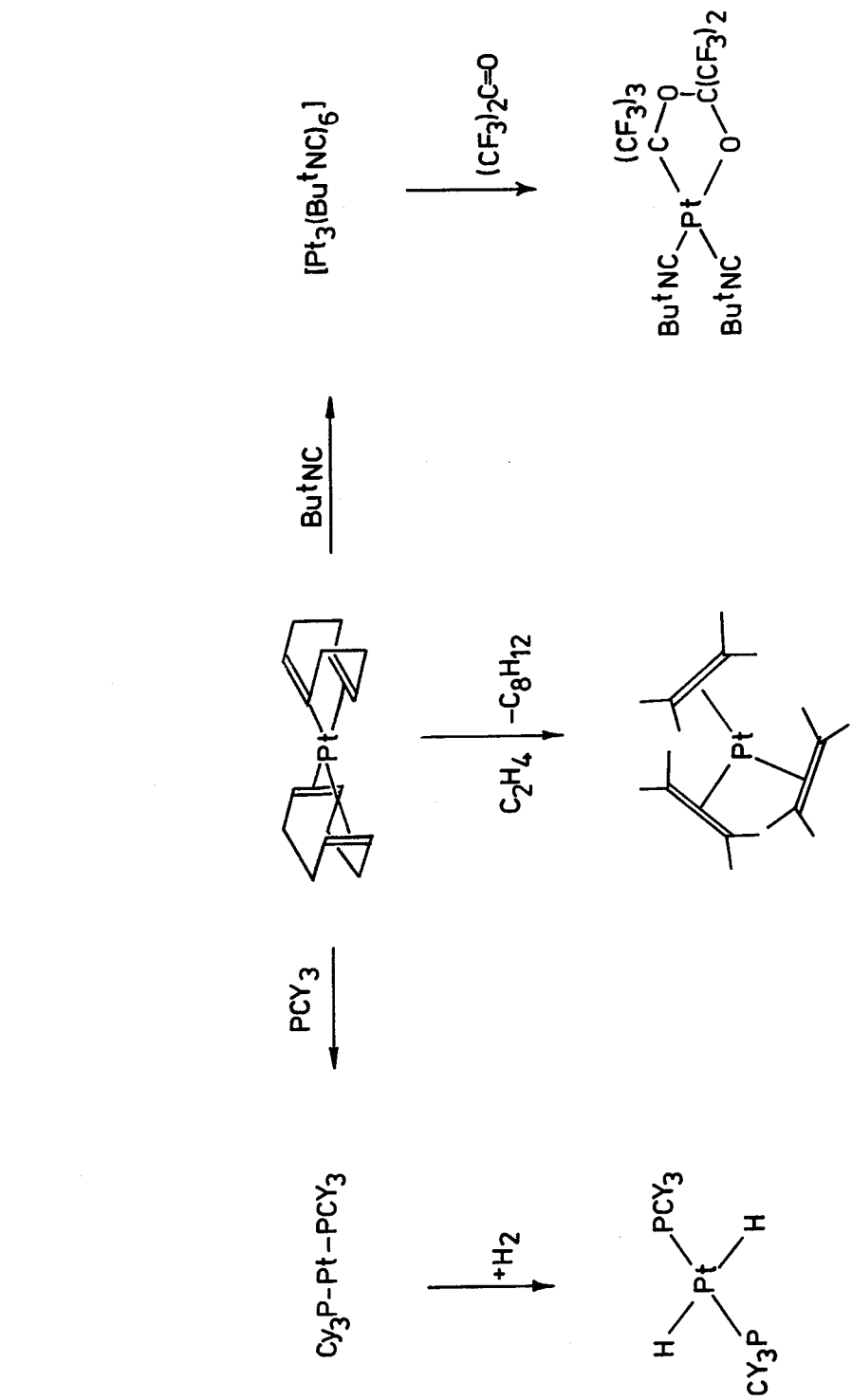

The reactions described in the above Examples are shown set out schematically in FIG. 2.

EXAMPLE 5

Preparation of bis(cis,cis-cyclo-octa-1,5-diene)palladium

A sample of the compound [PdCl$_1$(1,5-C$_8$H$_{12}$)] (2.85g. 10 mmol) was finely powdered and suspended in freshly distilled cis,cis-cyclo-octa-1,5-diene (15 cm$^3$). The mixture was degassed and cooled to −40° C and a solution of the lithium derivative of cyclooctatetraene (Li$_2$C$_8$H$_8$) (10 mmol) in diethyl ether was added over 5 minutes. at −30° C before being filtered through a short column (3 cm) of alumina at −30° C under an atmosphere of ethylene. The filtrate was collected in a tube cooled to −40° C. Careful removal of ethylene at reduced pressure caused the precipitation of a white material which, after decanting off the mother liquor, was washed with diethyl ether or butane at −30° C and dried under vacuum to give pure bis(cis,cis-cyclo-octa-1,5-diene)palladium. (Yield 60%).

Treatment of the product with bicyclo (2.2.1) heptene gave tris (bicyclo(2.2.1)heptene)palladium. Ethylene (1 atmos., −30°) displaces cyclo-octa-1,5-diene from bis(cyclo-octa-1,5-diene)palladium, as was observed with the analogous Pt(1,5-C$_8$H$_{12}$)$_2$, to give a highly reactive white crystalline complex, showing a $^1H$ n.m.r. resonance (d$^8$ -toluene, −60°) at T6.62(s). This complex is probably tris(ethylene)palladium, although present evidence does not exclude its formulation as (Pd(C$_2$H$_4$)$_4$).

EXAMPLE 6

Preparation of tricyclohexylphosphine bis(ethylene) palladium and platinum and trimethylphosphine bisethyleneplatium Addition of tricyclohexylphosphine to the white crystalline compound prepared in Example 5 gave tricyclohexylphosphine-bis(ethylene)palladium $^1H$ n.m.r. resonance (d$^8$-toluene, −35°) at 6.79 (s, CH$_2$=CH$_2$).

To a solution of the white crystalline complex (2 mmol), prepared in situ from $Pd(1,5\text{-}C_8H_{12})_2$ and ethylene in petroleum ether (40 cm$^3$) at $-30°$ C, was added a solution of tricyclohexylphosphine (2 mmol) in petroleum ether (10 cm$^3$). The solution was filtered through alumina into a tube cooled to $-78°$ C, giving white crystals of the product, tricyclohexylbis(ethylene)palladium, which were dried in a stream of ethylene at 0° C. (Yield 70%).

Similarly, there were prepared from trisethyleneplatinum and one molar equivalent of tricyclohexylphosphine and trimethylphosphine respectively, crystalline complexes tricyclohexylphosphinebis(ethylene)platinum [$^1$H n.m.r. resonances ($C_6H_6$, 35°) at 7.22 (s with $^{195}$Pt satellites, $CH_2$=$CH_2$, $J_{PtH}$58 Hz.) and 8.42 (br.m)] and trimethylphosphinebis(ethylene)platinum [$^1$H n.m.r. resonances ($C_6H_6$, 35°) at 7.32 (s with $^{195}$Pt satellites, $CH_6$=$CH_6$, $J_{PtH}$57 Hz.) and 8.78 (d with $^{195}$Pt satellites, PMe$_3$, $J_{PH}$8.5 Hz., $J_{PtH}$21.5 Hz.) $^{13}$C n.m.r. resonances (d$^8$-toluene) ($C_2H_4$ resonances only, +30°) $-36.7$ p.p.m. (s with $^{195}$Pt satellites, $J_{PtC}$152 Hz.); at $-40°$ two resonances were observed at $-33.6$ p.p.m. (d with $^{195}$Pt satellites, $J_{PC}$15.0 Hz., $J_{PtC}$158 Hz.) and $-38.6$ p.p.m. (d with $^{195}$Pt satellites, $J_{PC}$6.0 Hz., $J_{PtC}$137 Hz)].

These observation show that at room temperature trimethylphosphinebisethylene platinum is a fluxional molecule (as presumably also are the two tricyclohexylphosphine complexes) where it is likely the coordinated ethylene rotates about an axis through the metal and perpendicular to the C—C bond. The low temperature $^{13}$C spectrum of trimethylphosphinebisethyleneplatinum shows that the 'Frozen out' structure is again a trigonal planar arrangement. It is interesting to note that the activation energy for ethylene rotation in this complex is clearly higher than in tetrafluoroethylenebis(ethylene)platinum.

What we claim is:

1. A method of preparing bis(cis,cis-cyclo-octa-1,5 diene) platinum or palladium in which a reducing agent is allowed to react with [PtCl$_2$(1,5-C$_8$H$_{12}$)] or [PdCl$_2$(1,5-C$_8$H$_{12}$)] and excess cis, cis,cyclo-octa-1,5-diene in the presence of a solvent not having an active hydrogen atom.

2. Novel platinum and palladium complexes of the general formula:

$$(R_3{}^2E)_x(Q)_y M_m (R^1NC)_z$$

wherein Q is a radical containing at least one olefinic double bond or acetylenic triple bond; E is P, As, Sb or N; R$^2$ is aryl, alkyl or alkoxyl; M is Pt or Pd; x is 0, 1 or 2; R$^1$ is an alkyl or aryl group; x is 0 or 1; y is 0, 2 or 3; m is 1 or 3; z is 0 or 6; and when m is 3, then M is Pt, z is 6 and both x and y are 0; and when m is 1 and z is 0, then $x + y = 3$.

3. A method of preparing $R_3P$—Pt—$PR_3$ comprising reacting in solution bis (cis, Cis-Cyclo-octa-1,5 diene) platinum with the trisubstituted phosphine $R_3P$ wherein R is a bulky ligand such that not more than two of the phosphines can form a bond with the Pt atom.

4. A method of preparing

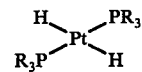

comprising reducing in solution $R_3P$—Pt—$PR_3$ with hydrogen wherein R is a bulky ligand such that not more than two of the phosphines $R_3P$ can form a bond with the Pt atom.

5. A method of preparing M(Q)$_3$ by reacting in solution bis(cis,cis-cyclo-octa-1,5 diene) M with the unsaturated compound Q in an inert solvent wherein M is Pt or Pd and Q is a radical containing at least one olefinic double bond or at least one acetylenic triple bond.

6. A method of preparing Pt$_3$(R$^1$NC)$_6$ by reacting in solution bis(cis, cis-cyclo-octa-1,5-diene) platinum with excess isonitrile R$^1$NC in an inert solvent wherein R$^1$ is an alkyl or aryl group.

7. A method of preparing $R_3E$ M (Q)$_2$ by reacting in solution M(Q)$_3$ with ER$_3$ in an inert solvent wherein M is Pt or Pd and Q is a radical containing at least one olefinic double bond or at least one acetylenic triple bond, E is P, As, Sb or N and R is aryl, alkyl, or alkoxyl.

8. A method of preparing Pt(Q)$_3$ or Pd(Q)$_3$ comprising reacting in solution [PtCl$_2$(1,5-C$_8$H$_{12}$)] or [PdCl$_2$(1,5-C$_8$H$_{12}$)] respectively with a reducing agent and the compound Q wherein Q is a radical containing at least one olefinic double bond or acetylenic triple bond.

9. A complex according to claim 2 wherein m is 3.

10. The complex of claim 2 wherein m is 1.

* * * * *

UNITED STATES PATENT AND TRADEMARK OFFICE
CERTIFICATE OF CORRECTION

PATENT NO. : 4,098,807
DATED : 4 July 1978
INVENTOR(S) : Francis Gordon Albert Stone, Michael Green, John Lionel Spencer It is certified that error appears in the above-identified patent and that said Letters Patent are hereby corrected as shown below:

Column 1, Lines 58-59
　　　　Delete "$R_3P$--P-t--$PR_3$" and substitute therefor -- $R_3P$--Pt--$PR_3$ --

Column 1, Lines 59-60
　　　　Delete "$R_3P$--P-d--$PR_3$" and substitute therefor -- $R_3P$--Pd--$PR_3$ --

Column 3, Line 30
　　　　Delete "Ca." and substitute therefor -- ca. --

Column 3, Line 40
　　　　Delete "5.80" and substitute therefor -- T5.80 --

Column 3, Line 64
　　　　Delete "threee" and substitute therefor -- three --

Column 3, Line 65
　　　　Delete "briding" and substitute therefor -- bridging --

Column 5, Line 1
　　　　Delete "$^{13}CF_2=CF_2$" and substitute therefor -- $^{13}CF_{-2}=CF_{-2}$ --

UNITED STATES PATENT AND TRADEMARK OFFICE
CERTIFICATE OF CORRECTION

PATENT NO. : 4,098,807

DATED : 4 July 1978

INVENTOR(S) : Francis Gordon Albert Stone, Michael Green, John Lionel Spencer

It is certified that error appears in the above-identified patent and that said Letters Patent are hereby corrected as shown below:

Column 5, Line 21
 Delete "H - C" and substitute therefor -- H - $\underline{C}$ --

Column 5, Line 22
 Delete "$CH_2$" and substitute therefor -- $\underline{C}H_2$ --

Column 5, Line 23
 Delete "C" and substitute therefor -- $\underline{C}$ -- (four times)

Column 6, Line 33
 Delete "$PdCl_1$" and substitute therefor -- $PdCl_2$ --

Column 7, Line 20
 Delete "$PMe_3$" and substitute therefor -- $PMe_{\underline{3}}$ --

Column 7, Line 26
 Delete "observation" and substitute therefor -- observations --

Column 7, Line 43
 Delete "allowed to react" and substitute therefor -- reacted in solution --

UNITED STATES PATENT OFFICE
CERTIFICATE OF CORRECTION

Patent No. 4,098,807                     Dated  July 4, 1978

Inventor(s)  Francis Gordon Albert Stone, Michael Green, John Lionel Spencer

It is certified that error appears in the above-identified patent and that said Letters Patent are hereby corrected as shown below:

Signed and Sealed this

Ninth Day of January 1979

[SEAL]

Attest:

RUTH C. MASON
Attesting Officer

DONALD W. BANNER
Commissioner of Patents and Trademarks